(12) United States Patent
Colliver et al.

(10) Patent No.: US 8,211,478 B2
(45) Date of Patent: *Jul. 3, 2012

(54) BEVERAGE PRECURSOR AND PROCESS FOR THE MANUFACTURE THEREOF

(75) Inventors: Steven Peter Colliver, Sharnbrook (GB); Ambalavanar Thiru, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 13 days.

This patent is subject to a terminal disclaimer.

(21) Appl. No.: 12/398,259

(22) Filed: Mar. 5, 2009

(65) Prior Publication Data

US 2009/0169705 A1 Jul. 2, 2009

Related U.S. Application Data

(62) Division of application No. 11/880,795, filed on Jul. 24, 2007, now abandoned.

(30) Foreign Application Priority Data

Jul. 24, 2006 (EP) ..................................... 06253867

(51) Int. Cl.
*A01N 65/00* (2009.01)
(52) U.S. Cl. ....................................................... 424/725
(58) Field of Classification Search .................. None
See application file for complete search history.

(56) References Cited

U.S. PATENT DOCUMENTS

| 3,821,440 | A * | 6/1974 | Reeve ............................ 426/312 |
| 6,432,467 | B1 * | 8/2002 | Blair et al. ..................... 426/597 |
| 7,553,509 | B2 * | 6/2009 | Dorr et al. ...................... 426/590 |
| 2002/0094360 | A1 | 7/2002 | Suzuki ............................. 426/83 |
| 2003/0096050 | A1 | 5/2003 | Inaoka et al. | |
| 2004/0028793 | A1 | 2/2004 | Inaoka et al. | |
| 2005/0129829 | A1 | 6/2005 | Hosoya et al. | |
| 2005/0163889 | A1 | 7/2005 | Yamada et al. | |
| 2005/0186314 | A1 | 8/2005 | Sasame et al. | |
| 2006/0093725 | A1 | 5/2006 | Zhang | |
| 2006/0121158 | A1 | 6/2006 | Ferruzzi et al. ................. 426/72 |

FOREIGN PATENT DOCUMENTS

| CA | 2 021 908 A | 2/1991 |
| EP | 1 514 476 | 3/2005 |
| EP | 1 527 694 | 5/2005 |
| EP | 1 297 757 | 6/2005 |
| EP | 1 557 097 | 7/2005 |
| EP | 1 695 629 | 8/2006 |
| EP | 1 297 749 | 5/2007 |

OTHER PUBLICATIONS

Saijo et al., 1999, 46(3), 138-147, Nippon Shokuhin Kagaku Koghaku Kaishi.*
European Search Report on Application No. EP 06 25 3867 dated Dec. 21, 2006.
Database WPI Week 200547, Derwent Publications Ltd., XP002412627 & JP 2005 168428.
Database WPI Week 200629, Derwent Publications Ltd., XP002412628 & JP 2006 094825.
Database WPI Week 200614, Derwent Publications Ltd., XP002412629 & WO 2006/008833.
Diepvens et al., "Metabolic effects of green tea and of phases of weight loss", Physiology and Behavior, vol. 87, No. 1, Jan. 30, 2006, XP005214249.
Amarowicz et al., "A Rapid Chromatolgraphic Method for Separation of Individual Catechins from Green Tea", Food Research International, Elsevier Applied Science, vol. 29, No. 1, 1996. pp. 71-76.
Patent Abstracts of Japan for Publication No. JP 11-000107.
T. Nagao et al., "Tea Catechins Suppress Accumulation of Body Fat in Humans", J. Oleo. Sci. 2001, 50(9), pp. 717-728 (Abstract only).
U. Peters et al., "Does tea affect cardiovascular disease? A Meta-Analysis" American Journal of Epidemiology, 2001, 154, pp. 495-503.
"Tea cultivation to Consumption", K.C. Willson and M.N. Clifford (Eds), 1$^{st}$ Edn. 1992, Chapter 13, pp. ix-xi, , 414, 422-423, 463, 483-487, 636-637, 654-655, 700-701, 764-765.
Aurateas, "Introduction to Tea 76", Introduction to Tea, 2008, 3 pages.

* cited by examiner

*Primary Examiner* — Michael Meller
(74) *Attorney, Agent, or Firm* — Ellen Plotkin

(57) ABSTRACT

The present invention provides a beverage precursor comprising tea material and food-grade additive, wherein the beverage precursor is present in an amount wherein contact of the beverage precursor with 250 ml water for 2 minutes at 90° C. produces a beverage comprising catechins in an amount of between 0.05% and 2% by weight of the beverage. The present invention also provides a process for manufacturing a beverage precursor comprising macerating tea leaf and/or stem with a rotorvane and at least one CTC process.

1 Claim, No Drawings

BEVERAGE PRECURSOR AND PROCESS FOR THE MANUFACTURE THEREOF

This application is a Divisional of Ser. No. 11/880,795 filed Jul. 24, 2007, now pending.

TECHNICAL FIELD OF THE INVENTION

The present invention relates to beverage precursors for preparing tea-based beverages.

BACKGROUND OF THE INVENTION

Green tea is a popular beverage which has been consumed in China and Japan for many hundreds of years. Recently, extensive laboratory research and epidemiologic studies have shown that compounds present in green tea (particularly catechins) may reduce the risk of a variety of illnesses. Furthermore, catechins have been shown to suppress accumulation of visceral fat and so may be useful in controlling bodyweight and bodyshape (see, for example, T. Nagao et al., "Tea Catechins Suppress Accumulation of Body Fat in Humans", *J. Oleo. Sci.*, 2001, 50(9), pp. 717-728). These studies, along with the increasing complexity of the consumer's palate have led to growth in the consumption of green tea, even in markets (such as the USA and Western Europe) where there is no tradition of green tea consumption.

Although, some of the health benefits of tea may be apparent at consumption rates as low as three cups per day (see, for example, U. Peters et al., "Does tea affect cardiovascular disease? A meta-analysis.", *American Journal of Epidemiology*, 2001, 154, pp. 495-503), many individuals do not even achieve this modest consumption rate on a long term basis. Furthermore, tea beverages are less convenient to prepare than beverages prepared from non-tea-based beverage precursors, such as instant coffee, owing to the relatively slow rate of infusion of tea leaves and slow rate of dissolution of tea powders.

Thus we have recognised that there is a need to provide beverage precursor in a form which is both convenient for everyday use and which may allow a consumer to obtain the necessary intake of catechins from a fewer number of beverages than would need to be prepared from conventional beverage precursors.

We have found that such a need may be met by providing beverage precursor in a specific amount and with a specific composition. We have also recognised that there is a need for a process specifically adapted to manufacture such a beverage precursor.

TESTS AND DEFINITIONS

Beverage

As used herein the term "beverage" refers to a substantially aqueous drinkable composition suitable for human consumption.

Beverage Precursor

A beverage precursor is defined as a fabricated composition suitable for preparing a beverage.

As used herein, the term "packaged" means that the beverage precursor is contained within a sealed packet.

Tea Material

As used herein, the term "tea material" refers to dry material from the plant *Camellia sinensis* var. *sinensis* and/or *Camellia sinensis* var. *assamica*. The material may have been subjected to a so-called "fermentation" step wherein it is oxidised by certain endogenous enzymes that are released during the early stages of "black tea" manufacture. This oxidation may even be supplemented by the action of exogenous enzymes such as oxidases, laccases and peroxidases. Alternatively the material may have been partially fermented ("oolong" tea) or substantially unfermented ("green tea").

The term "tea leaves and/or stem" refers to tea material that is derived from the leaves and/or stem of the plant, and that has not been subjected to an extraction step (i.e., infusible tea material). The term "tea extract" refers to tea material that has been extracted from tea leaves and/or stem, and which is soluble in boiling water.

Tea-Based Beverage

As used herein, the term "tea-based beverage" refers to a beverage comprising at least 0.01% by weight dissolved tea material.

Food-Grade Additive

As used herein, the term "food-grade additive" refers to edible material that is not derived from a plant of the species *Camellia sinensis*.

Catechins

As used herein the term "catechins" is used as a generic term for catechin, gallocatechin, catechin gallate, gallocatechin gallate, epicatechin, epigallocatechin, epicatechin gallate, epigallocatechin gallate, and mixtures thereof.

Determination of Catechins and Caffeine in Tea Material

The amounts of catechins and caffeine in tea material are determined simultaneously by reverse-phase HPLC as follows:

Sample Preparation for Tea Leaves and/or Stem

1. Grind tea material using a Cyclotech™ 1093 sample mill (FOSS Ltd, Warrington, Cheshire, UK) fitted with a 0.5 μm screen, until a fine powder is achieved.

2. Weigh accurately approximately 200 mg of the ground tea material into an extraction tube, and record the mass.

3. Warm at least 20 ml of a methanol-water solution (70% v/v methanol in distilled water) to 70° C.

4. Add 5 ml of the hot methanol-water solution to the extraction tube. Gently mix the methanol-water and tea material on a vortex mixer; place in a water bath at 70° C. for 5 minutes; mix again and then place in a water bath at 70° C. for a further 5 minutes.

5. Gently mix the methanol-water and tea material on a vortex mixer again and then allow too cool for a 10 minutes at an air temperature of 20° C.

6. Centrifuge the extraction tube at a relative centrifugal force (RCF) of 2900 g for 10 minutes.

7. The extraction tube should now contain a liquid supernatant on top of a plug of tea material. Carefully decant supernatant into a clean graduated test tube.

8. Add 5 ml of the hot methanol-water solution to the plug in the extraction tube. Gently mix the methanol-water and tea material on a vortex mixer; place in a water bath at 70° C. for 5 minutes; mix again and then place in a water bath at 70° C. for a further 5 minutes.

9. Gently mix the methanol-water and tea material on a vortex mixer again and then allow too cool for a 10 minutes at an air temperature of 20° C.

10. Centrifuge the extraction tube at a RCF of 2900 g for 10 minutes.

11. The extraction tube should now contain a liquid supernatant on top of a plug of tea material. Carefully decant supernatant into the graduated test tube containing the supernatant from step 7.

12. Make up the pooled supernatants to 10 ml with the methanol-water solution.

13. Add 1 ml of a solution of 2.5 mg/ml EDTA and 2.5 mg/ml ascorbic acid in distilled water to the graduated test tube.

14. Dilute 1 part of the pooled supernatant mixture with 4 parts (by volume) of 10% acetonitrile stabiliser solution (10% v/v acetonitrile, 0.25 mg/ml ascorbic acid and 0.25 mg/ml EDTA in distilled water).

15. Decant the diluted pooled supernatant mixture into microcentrifuge tubes and centrifuge in a bench top centrifuge at a RCF of 14000 g for 10 minutes.

Sample Preparation for Tea Extract

1. Weigh accurately approximately 190 mg of tea extract into a glass vial.

2. Add the correct amount of 10% acetonitrile stabiliser solution (10% v/v acetonitrile, 0.25 mg/ml ascorbic acid and 0.25 mg/ml EDTA in distilled water) to give a final concentration of tea extract of 20 mg/ml.

3. Ensure that the tea extract is dissolved.

4. Dilute 1 part of the tea extract solution with 4 parts (by volume) of 10% acetonitrile stabiliser solution (10% v/v acetonitrile, 0.25 mg/ml ascorbic acid and 0.25 mg/ml EDTA in distilled water).

4. Decant the dilute tea extract solution into microcentrifuge tubes and centrifuge at a RCF of 14000 g for 10 minutes.

HPLC Analysis Conditions
Column: Luna Phenyl hexyl 5μ, 250×4.60 mm
Flow rate: 1 ml/min
Oven temperature: 30° C.
Solvents: A: 2% acetic acid in acetonitrile
B: 2% acetic acid and 0.02 mg/ml EDTA in water
Injection volume: 10 μl
Gradient:

| Time | % Solvent A | % Solvent B | Step |
|---|---|---|---|
| 0 to 10 min | 5 | 95 | Isocratic |
| 10 to 40 min | 5-18 | 95-85 | Linear gradient |
| 40 to 50 min | 18 | 82 | Isocratic |
| 50 to 55 min | 50 | 50 | Wash |
| 55 to 75 min | 5 | 95 | Isocratic |

Quantification: Peak area relative to a calibration curve constructed daily. Calibration curve is constructed from caffeine and the concentration of catechins is calculated using the relative response factors of the individual catechins to caffeine (from the ISO catechin method—ISO/CD 14502-2). Individual caffeine standards (Sigma, Poole, Dorset, UK) are used as peak identification markers.

Determination of Catechins and Caffeine in a Beverage Produced By Contacting Beverage Precursor with 250 ml Water at 90° C. for 2 Minutes The amounts of catechins and caffeine delivered by a beverage precursor are determined simultaneously by reverse-phase HPLC as follows:

Sample Preparation

1. For beverage precursor contained in an infusion package, the whole infusion package is placed in a 500 ml container. For beverage precursor not in an infusion package, the beverage precursor is removed from any package and placed in a 500 ml container.

2. 1 litre of deionised water is then brought to boiling and 250 g immediately added to the 500 ml container.

3. The container is stored at an air temperature of 20° C. and the beverage precursor is allowed to statically infuse/dissolve in the water.

4. After 2 minutes, remaining beverage precursor is removed from the container. In the case of a beverage precursor contained in an infusion package, the infusion package is simply removed from the liquid in the container. In the case of beverage precursor not in an infusion package, the liquid is strained through muslin.

5. 9 ml of the liquid are then taken and 1.12 ml of acetonitrile added, along with 1.12 ml of a solution of 2.5 mg/ml EDTA and 2.5 mg/ml ascorbic acid in distilled water.

6. The resulting solution is then decanted into microcentrifuge tubes and centrifuged at a RCF of 14000 g for 10 minutes.

HPLC Analysis Conditions

The HPLC analysis conditions are identical to those given above for the tea material.

SUMMARY OF THE INVENTION

In a first aspect, the present invention provides a beverage precursor comprising tea material and food-grade additive, the beverage precursor being present in an amount wherein if the beverage precursor is contacted with 250 ml water for 2 minutes at 90° Cc a beverage would be produced comprising catechins in an amount of between 0.05 and 2% by weight of the beverage.

The beverage precursor of the invention is provided in an amount that allows for consumers to meet the daily intake of catechins required to achieve health benefits, whilst requiring shorter time to prepare a beverage and/or preparation of fewer beverages per day compared with conventional beverage precursors.

The efficiency of catechin delivery may be further improved if the beverage precursor is present in an amount wherein the contact of the beverage precursor with 250 ml water for 2 minutes at 90° C. produces a beverage comprising catechins in an amount of at least 0.06% by weight of the beverage, more preferably at least 0.07% and most preferably at least 0.08%. The efficiency of catechin delivery should not be too high, however, otherwise the taste and/or appearance of the beverage may be impaired. Therefore it is preferred that the beverage precursor is present in an amount wherein contact of the beverage precursor with 250 ml water for 2 minutes at 90° C. produces a beverage comprising catechins in an amount of less than 1% by weight of the beverage, more preferably less than 0.5% and most preferably less than 0.2%.

The mass of beverage precursor required to deliver suitable amounts of catechins to a beverage will depend upon the catechin content of the beverage precursor and on the solubility of the catechins in the aqueous medium used to prepare the beverage. It is preferred, however, that the mass of beverage precursor is at least 0.5 g, as smaller amounts are difficult to accurately portion and dose. More preferably the mass is at least 0.7 g, and most preferably at least 0.9 g. Preferably also, the mass of beverage precursor is less than 5 g as larger amounts become inconvenient to store and/or handle. More preferably the mass is less than 4 g, most preferably less than 3 g.

In order to provide maximum rate of infusion and/or dissolution of the tea material, it is preferred that the tea material is particulate. Preferably also, at least 95% (more preferably from 98 to 100%) by weight of the particulate tea material has a maximum linear dimension of less than 2 mm. In particular, it is preferred that at least 95% (more preferably from 98 to 100%) by weight of the particulate tea material has a mesh size below 9 (i.e. passes through a Tyler Mesh of No. 9).

Green tea contains a higher level of catechins than semi-fermented tea or fermented tea and so it is preferred that the tea material comprises green tea material. More preferably the tea material comprises at least 75% by weight green tea material, most preferably from 90 to 100%.

The tea material preferably comprises a high level of catechins, thus it is preferred that the tea material comprises at least 10% catechins by weight of the tea material, more preferably at least 12% and most preferably at least 13%. It is also preferred, however, that the tea material comprises further compounds that deliver the taste and benefits of tea and so it is preferred that the level of catechins in the tea material is less than 90% by weight of the tea material, more preferably less than 70% and most preferably less than 30%. These further compounds include theaflavins, thearubigins, gallic acid, theanine, caffeine, quinic acid, oxalic acid, potassium ions, sodium ions, magnesium ions, aluminium ions, sucrose, glucose, maltose, fructose, pectin, or mixtures thereof.

Caffeine is particularly preferred as it has been shown to assist in body management, especially in weight control and/or control of body shape. Thus it is preferred that the tea material comprises caffeine in an amount of at least 1% by weight of the tea material, more preferably at least 2% and most preferably at least 3%. Too much caffeine, however, may result in an unpalatable beverage and/or unwanted physiological effects. Thus it is also preferred that the tea material comprises less than 25% caffeine by weight of the tea material, more preferably less than 15% and most preferably less than 7%.

To provide maximum benefit from the catechins and caffeine in terms of body management, it is preferred that the amount of beverage precursor is such that the beverage produced by contacting the beverage precursor with 250 ml water for 2 minutes at 90° C., comprises caffeine in an amount of between 0.005 and 0.5% by weight of the beverage, more preferably between 0.01 and 0.2% and most preferably between 0.015 and 0.1%. Preferably also, the amount of beverage precursor is such that the beverage produced by contacting the beverage precursor with 250 ml water for 2 minutes at 90° C. has a weight ratio of catechins to caffeine of less than 6:1, more preferably in the range 4.9:1 to 1:1, most preferably between 4.5:1 and 2:1.

The beverage precursor of the present invention comprises food grade additive. The presence of the food-grade additive may help in providing high efficiency of catechin delivery to a beverage. This is because the food-grade additive may help to separate the tea material and thus allow for increased rate of infusion and/or dissolution of the tea material. The food grade additive may additionally or alternatively help to mask the bitter taste associated with catechins. Thus it is preferred that the beverage precursor comprises tea material and food-grade additive in a weight ratio of less than 100:1, more preferably less than 50:1 and most preferably less than 30:1. However, in order to maximise the benefits and taste provided by the tea material, it is preferred that the weight ratio of tea material to food-grade additive in the precursor is at least 1:2, more preferably at least 2:1 and most preferably at least 5:1.

The ability of the food-grade additive to separate the tea material and thus allow for increased rate of infusion and/or dissolution of the tea material is enhanced when the food-grade additive is particulate. Thus it is preferred that the food-grade additive is particulate. Preferably also, at least 95% (more preferably from 98 to 100%) by weight of the food-grade additive has a maximum linear dimension of less than 2 mm. In particular, it is preferred that at least 95% (more preferably from 98 to 100%) by weight of the food-grade additive has a mesh size below 9 (i.e. passes through a Tyler Mesh of No. 9).

The food-grade additive may be any edible material and may, for example, comprise saccharide (including sugars, oligosaccharides and/or polysaccharides), salt, sweetener (including artificial sweeteners such as aspartame, sucralose, and/or acesulfame K), protein, milk powder, food acid (and/or a salt thereof), flavour or a mixture thereof. Particularly preferred are sugars, oligosaccharide, sweetener, salt and mixtures thereof, owing to their ability to mask the bitterness of catechins.

Suitable flavours include natural and synthetic fruit flavours, and/or natural or synthetic herb flavours. Examples of fruit flavours include apple, peach, pear, lemon, lime, mandarin, grapefruit, cranberry, orange, strawberry, grape, kiwi, pineapple, passion fruit, mango, guava, raspberry and cherry. Examples of herb flavours include jasmine, chamomile, rose, mint, hawthorn, chrysanthemum, osmanthus, hibiscus, elderflower and verbena. Surprisingly, we have found that pineapple flavour (natural or synthetic) is particularly effective at masking the bitterness of catechins, therefore it is particularly preferred that the flavour comprises pineapple flavour. The pineapple flavour may be natural or synthetic. Preferably the pineapple flavour comprises 2-propenyl hexanoate.

The food-grade additive may additionally or alternatively comprise a weight management active. Suitable actives include biotin, pantothenic acid (vitamin B5), vitamin B6, niacin, magnesium, yerba mate extract, guarana extract, hydroxycitric acid and mixtures thereof.

The beverage precursor is preferably packaged in the said amount. The packet may be any suitable food-grade package.

In one embodiment the packet is water-resistant. Suitable water-resistant materials are known in the art and include foil, waxed-paper and laminate materials. In this embodiment, the beverage precursor is removed from the packet in order to prepare a beverage. This embodiment is particularly preferred when the tea material is substantially free from tea leaf and/or stem. For example, the tea material may comprise at least 95% tea extract by weight of the tea material, more preferably at least 98% and most preferably from 99.5 to 100%.

In another embodiment the package is an infusion package. This embodiment is especially convenient when the tea material comprises tea leaf and/or stem. For an infusion package, the packet is of porous material. The porous material can be any material that is suitable for enabling water to infuse within the packet without allowing any insoluble contents to leave the packet, for example filter paper, nylon mesh, gauze, muslin, nonwoven fabric or some other similar material or fabric.

The use of tea leaf and/or stem in the tea material is particularly preferred as tea leaf and/or stem is not produced with the intensive processing such as is involved in manufacture of tea extract. As a result, tea leaf and/or stem has a more natural flavour and comprises a wider range of natural tea components than refined forms of tea material. Therefore, in a preferred embodiment, the tea material comprises tea leaf and/or stem in an amount of at least 90% by weight of the tea material, more preferably at least 95% and most preferably from 98 to 100%.

The tea leaf and/or stem is preferably green tea leaf and/or stem. Preferably also, the tea leaf and/or stem comprises catechins in an amount of at least 10% by weight of the leaf and/or stem, more preferably at least 12% and most between 13 and 25%.

Of the two varieties of the tea plant *Camellia sinensis*, the variety *Camellia sinensis* var. *assamica* typically has the highest level of catechins. Furthermore, var. *assamica* is relatively rich in certain non-flavanol actives, such as the amino acid theanine. However, because catechins have a large influence on the bitterness and astringency of tea infusions, var. *assamica* is conventionally considered unsuitable for use in green tea production (see, for example, "Tea: Cultivation to Consumption", K. C. Willson and M. N. Clifford (Eds), 1$^{st}$ Edn, 1992, Chapman & Hall (London), Chapter 13, p. 414). We have found, however, that var. *assamica* is particularly suitable for providing the tea material of the present invention, especially as the food-grade additive may help to mask the bitterness of the catechins. Thus it is preferred that the tea leaf and/or stem comprises at least 90% by weight of material from *Camellia sinensis* var. *assamica*, more preferably at least 95% and most preferably from 98 to 100%.

Conventional manufacture of tea leaf and/or stem involves a maceration step. Maceration involves wounding the leaves and/or stem prior to drying. The wounding is usually affected by rolling and/or crushing the leaves and/or stem i.e. to break down the plant tissue structure. In order to maximise this wounding and the amount of catechins released by the tea material, it is preferred that tea leaves and/or stem used in the beverage precursor of the present invention have been produced by a process wherein fresh tea leaves and/or stem are macerated by passing through a cutting machine. Most preferred is that the tea leaf and/or stem has been macerated using a CTC process. "CTC" comes from the words "crush, tear and curl". CTC machines and processes are well-known to those skilled in the art (see, for example, "Tea: Cultivation to Consumption", K. C. Willson and M. N. Clifford (Eds), 1$^{st}$ Edn, 1992, Chapman & Hall (London), Chapter 14, pp. 483-485). Even more preferred is maceration using a combination of a rotorvane and CTC process. Rotorvanes are also well-known to those skilled in the art and are also described in Chapter 14 of "Tea: Cultivation to Consumption" (especially pp. 486-487). Maceration with the combination of rotorvane and CTC processes results in good catechin delivery and provides the tea material in a granular form which is especially convenient for combining with food-grade additive. A particularly effective process involves macerating the tea leaf and/or stem with a rotorvane followed by two passes through a CTC process.

The tea material may comprise a mixture of tea leaves and/or stem with tea extract.

The beverage precursor is preferably dry. In particular, it is preferred that the beverage precursor comprises less than 15% water by weight of the beverage precursor, more preferably less than 10% and most preferably from 5 to 0.1%.

In a further aspect, the present invention provides a method of manufacturing a beverage comprising contacting the beverage precursor with an aqueous medium. Suitable amounts of aqueous medium range from 50 g to 1000 g, more preferably 150 g to 500 g, most preferably 175 g to 300 g. The aqueous medium preferably comprises at least 90% water by weight of the aqueous medium, more preferably at least 98%, most preferably from 99.8 to 100%.

The beverage precursor of this invention and/or the beverage may be used as a medicament or in the preparation of a medicament. In particular, the beverage precursor and/or beverage may be used to provide any of the benefits associated with consumption of catechins such as treating and/or preventing cancer; and/or treating and/or preventing cardiovascular disease. It is particularly preferred to use the beverage precursor and/or beverage for controlling the bodyweight and/or shape of an individual. For example, the beverage precursor or beverage may be used in a method of providing at least one of these benefits to an individual, the method comprising administering to the individual the beverage. Preferably the beverage is administered orally.

In a still further aspect, the present invention provides a process for manufacturing a beverage precursor comprising the steps of:
  a) providing fresh tea leaf and/or stem; then
  b) heat-treating the fresh leaf and/or stem to arrest enzyme action; then
  c) macerating the fresh leaf and/or stem with a rotorvane and at least one CTC process; then
  d) drying the macerated leaf and/or stem; then
  e) optionally sorting the dried macerated leaf and/or stem according to particle size; and
  f) combining the macerated leaf and/or stem with food-grade additive, preferably particulate food-grade additive.

The process is preferably used to manufacture the beverage precursor of the first aspect of the invention.

DETAILED DESCRIPTION

The present invention will be further described with reference to the following examples.

EXAMPLE 1

Fresh tea leaf (two leaves and a bud) from *Camellia sinensis* var. *assamica* was harvested from fields in Kenya. The fresh leaf has a moisture content of 76-80% by weight. The fresh leaf was then air-dried to a leaf moisture content of 75(±1)%. The leaf was then steamed for 60 seconds at a temperature of 96° C. to inactivate any endogenous enzymes and thus prevent fermentation. The moisture content of the steamed leaves was then reduced to 67(±1)% by passing the leaf through two hot air drum driers in series followed by a vibratory bed hot air drier.

Leaf at the end of the vibratory bed was cooled to room temperature (~25° C.) and then fed to a rotorvane. Macerated leaf from the rotorvane was then fed through two CTC machines in series. After the CTC processing, the macerated leaf was dried in a fluid bed drier to a moisture content of below 3%.

Fibres and the secondaries were then removed from the tea leaf and the leaf sieved. The sorted leaf had a size range of −10+40 mesh (Tyler), a content of catechins of 13.3% by weight and a caffeine content of 2.9% by weight.

The tea leaf was then blended with a flavour composition, dosed into pyramid tea bags and the tea bags sealed. Each tea bag contained 1.9 g of tea leaf and 0.2 g of the flavour composition. The flavour composition was a granular mixture of maltodextrin (carrier) with pineapple and hibiscus aroma. The pineapple aroma comprised 2-propenyl hexanoate.

Infusion of a tea bag in 250 ml water at 90° C. for 2 mins produced a beverage with a content of catechins of 0.082% by weight and a caffeine content of 0.020% by weight.

EXAMPLE 2

Tea bags were made using the same process as that described in Example 1 except that the way in which the tea leaf was macerated was varied. For Test A, maceration consisted of passing the leaf through three CTC machines in series; for Test B, maceration consisted of passing the leaf through two CTC machines in series and for Test C the leaf was macerated as in Example 1, i.e. by passing the fresh leaf through a rotorvane and then two CTC machines in series.

Table 1 shows the appearance of the leaf for each of Tests A, B and C. Also shown in Table 1 is the infusion performance in terms of total solids solubilised when a tea bag is infused under identical conditions for each of Tests A, B and C.

|  | Test A (3 × CTC) | Test B (2 × CTC) | Test C (Rotorvane + 2 × CTC) |
|---|---|---|---|
| Leaf Appearance | dusty/open | dusty/open | granular |
| Total soluble solids (mg/l) | 3.4 | 3.9 | 4.0 |

The invention claimed is:

1. A process for manufacturing a beverage precursor of *Camellia sinensis* var. *assamica* consisting essentially of:
   a) providing fresh leaf, stem and bud of *Camellia sinensis* var. *assamica*;
   b) heat-treating the fresh leaf, stem and bud to arrest enzyme action;
   c) passing the leaf, stem and bud through a rotorvane to produce partially macerated leaf, stem and bud;
   d) passing the partially macerated leaf, stem and bud twice through a CTC machine;
   e) drying the macerated leaf, stem and bud to yield dried macerated leaf, stem and bud;
   f) sorting the dried macerated leaf, stem and bud according to particle size thereby producing macerated leaf, stem and bud that is in granular form;
   g) combining the macerated leaf, stem and bud in granular form with maltodextrin; and
   h) packaging the combined granular form of macerated leaf, stem and bud in an infusion package.

* * * * *